(12) United States Patent
Macduff

(10) Patent No.: US 8,337,568 B2
(45) Date of Patent: Dec. 25, 2012

(54) MECHANICAL PROSTHETIC FINGER DEVICE

(76) Inventor: Charles Colin Macduff, Olympia, WA (US)

( * ) Notice: Subject to any disclaimer, the term of this patent is extended or adjusted under 35 U.S.C. 154(b) by 0 days.

(21) Appl. No.: 13/183,005

(22) Filed: Jul. 14, 2011

(65) Prior Publication Data

US 2012/0303136 A1    Nov. 29, 2012

Related U.S. Application Data

(60) Provisional application No. 61/364,227, filed on Jul. 14, 2010.

(51) Int. Cl.
*A61F 2/54* (2006.01)

(52) U.S. Cl. .......................................................... 623/64

(58) Field of Classification Search ............... 623/63–64
See application file for complete search history.

(56) References Cited

U.S. PATENT DOCUMENTS

| | | | | |
|---|---|---|---|---|
| 2,706,296 | A * | 4/1955 | Fletcher et al. | 623/64 |
| 6,908,489 | B2 * | 6/2005 | Didrick | 623/64 |
| 2004/0054424 | A1 * | 3/2004 | Matsuda | 623/64 |
| 2006/0224249 | A1 * | 10/2006 | Winfrey | 623/64 |

* cited by examiner

*Primary Examiner* — Bruce E Snow
(74) *Attorney, Agent, or Firm* — Sinorica, LLC

(57) ABSTRACT

A prosthetic finger that is able to provide independent natural movement to mimic a real finger. The present invention utilizes unique connections to provide users with natural movement and restore their ability to perform activities that require the full dexterity of their hands. Additionally, the present invention also allows users to interact with touch screens that normally would not work due to the insulating properties of other traditional prosthetic fingers.

20 Claims, 4 Drawing Sheets

MECHANICAL PROSTHETIC FINGER DEVICE

The current application claims a priority to the U.S. Provisional Patent application Ser. No. 61/364,227 filed on Jul. 14, 2010.

FIELD OF THE INVENTION

The present invention relates generally to a prosthetic device. More specifically, the present invention is a prosthetic device designed for full finger, partial finger, or finger tip amputees.

BACKGROUND OF THE INVENTION

If a person loses a finger, a finger segment, or a finger tip, the result is impaired performance of the hand. Having an amputated finger inhibits an amputee from performing some of the most basic tasks. For example, with a lost finger or finger tip, the task of typing on a computer or simply dialing on a phone becomes significantly difficult. These types of tasks requires the actions with precision that only fingers are able to offer. Not only do fingers allow people to perform precise actions, but fingers also provide people with a increased ability to handle items. While holding an item in one hand, the weight of the item is dispersed through all of a users fingers. By simply varying the force used by each fingers on the holder's hands, the holder is able to manipulate the item in a myriad of ways. However, if the holder is missing a single finger, the amount of precision for the manipulation and the number of ways the holder can manipulate the item is decreased. The present invention is a device that acts as a prosthetic substitute of the lost portion of a finger. The present invention is designed to bend and naturally mimic a real finger. Additionally, the present invention comprises a metal thread looped about the tip of the finger to allow the users to interact with a capacitive type of touch screen.

DETAIL DESCRIPTIONS OF THE INVENTION

Figure 1:
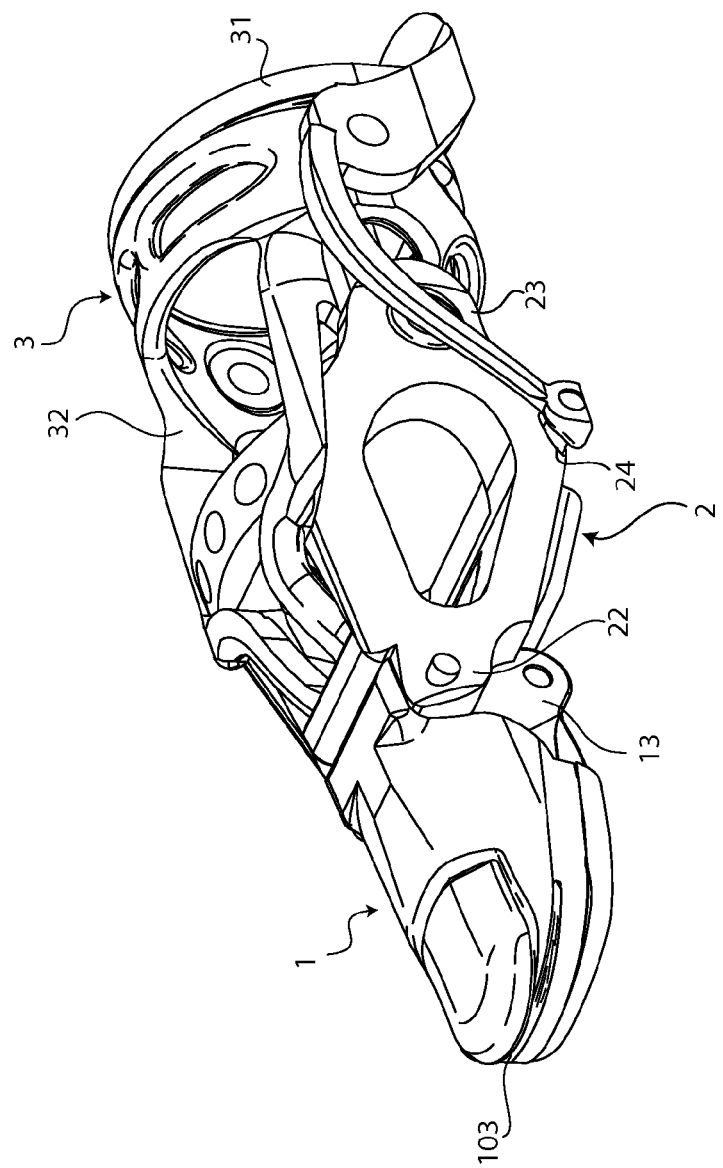
FIG. 1 is a perspective view of the present invention.

All illustrations of the drawings are for the purpose of describing selected versions of the present invention and are not intended to limit the scope of the present invention.

The present invention is a prosthetic finger, that can be fitted for a user with an amputated finger, finger tip, or finger segment. The prosthetic finger is a mechanical finger that is able to mimic the motions and functionalities of a real finger. The mechanical prosthetic finger comprises of three major components including a distal phalange 1, a middle phalange 2, and a proximal phalange ring 3. A plurality of rods 8 and a series of hinges are used to secure the distal phalange 1, the middle phalange 2, and the proximal phalange ring 3 together. The distal phalange 1 is the tip segment of the prosthetic finger. The middle phalange 2 is the middle segment of the prosthetic finger. The proximal phalange ring 3 is the base of the prosthetic finger that anchors the entire prosthetic finger to the user's residual finger. As the level of amputation differs among each user, the present invention can be modified to be custom fit for each user. For example, users who have an amputated finger tip will be custom fitted with a prosthetic finger, where the middle phalange 2 and the proximal phalange ring 3 are frames that fit and mount to the user's residual finger. To provide the prosthetic finger with grip and a softer touch, the present invention additionally comprises a distal pad platform 4, a distal pad 5, a middle pad platform 6, and a middle pad 7. The distal pad 5 and the middle pad 7 are made from a soft texture that mimics the texture of a real finger. In the preferred embodiment of the present invention, to additionally contribute to the realistic aspect of the prosthetic finger, the present invention further comprises of a articulation cable 9 and a touch screen mechanism 10. The articulation cable 9 further provides the prosthetic finger with realistic curling motions. The touch screen mechanism 10 allows the user to use the prosthetic finger to operate touch screens. Although some touch screens, such as resistive touch screens, only require pressure for sensing the touch, other touch screens uses the body's natural current to sense touch. These touch screens that require the user's natural body current are called capacitive touch screens. The touch screen mechanism 10 allows the user to conduct their own body current and direct it towards the tip of the prosthetic finger.

Figure 2:
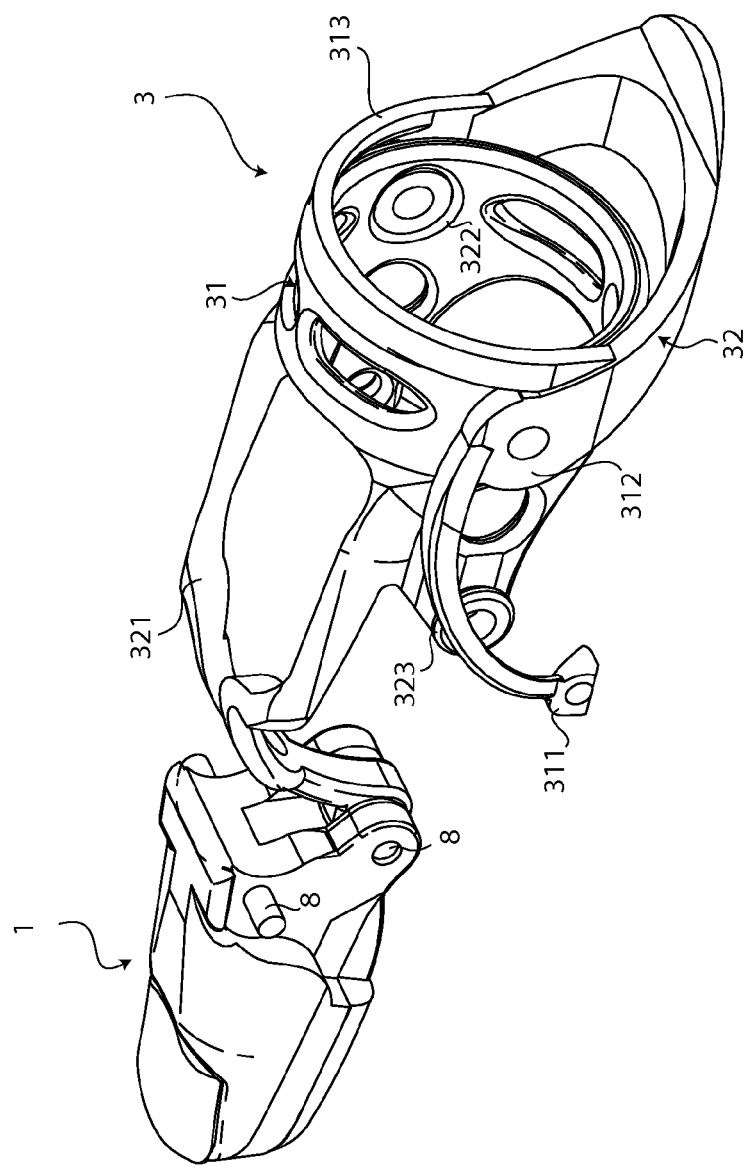
FIG. 2 is a view of the present invention without the middle phalange showing the connection of the extended wishbone hinge to the pair of proximal pulling hinges.
Figure 3:
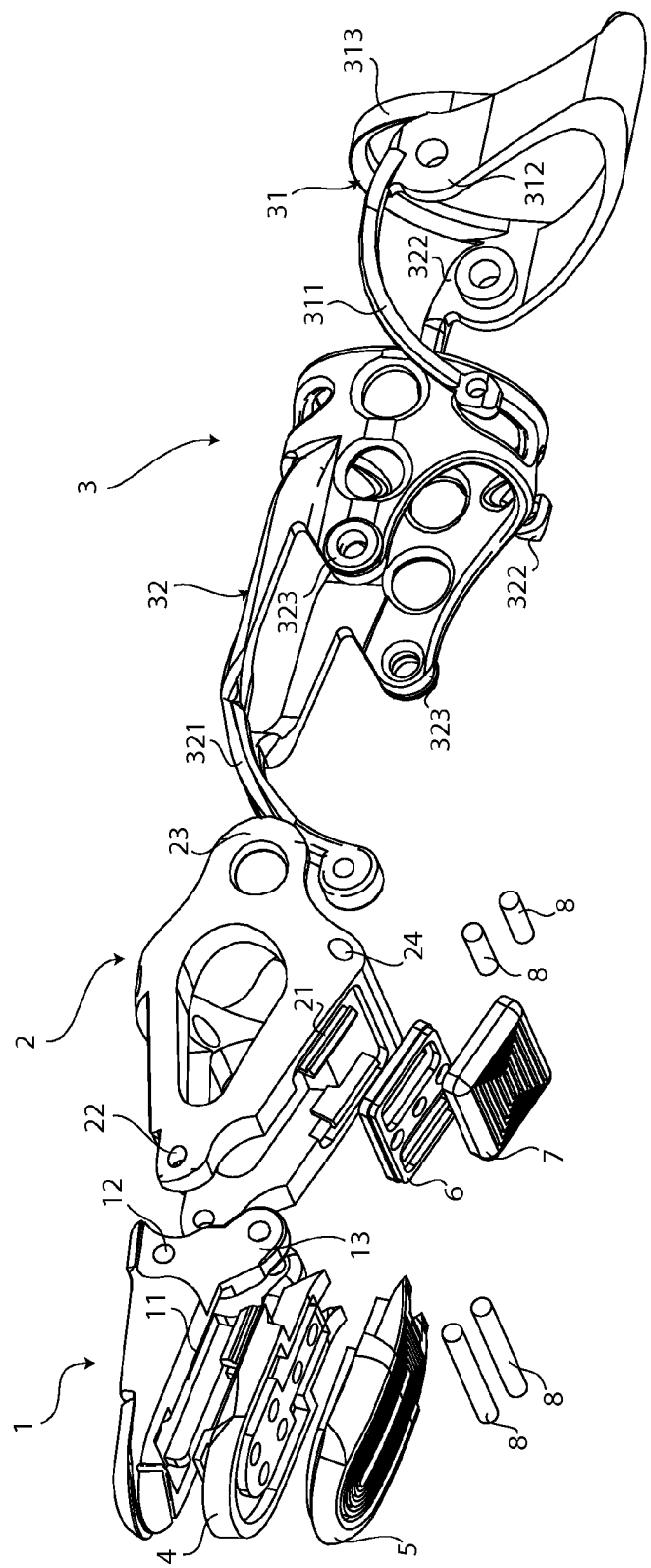
FIG. 3 is an exploded view of the present invention.

In reference to FIGS. 1-3, the distal phalange 1 comprises a distal platform fastener 11, a middle phalange joint channel 12, and a pair of proximal pulling hinge. The distal pad 5 and the distal pad platform 4 are secured to the distal phalange 1. The distal pad 5 is engaged and adhered to the distal pad platform 4 by a RTV silicone adhesive. The use of such an adhesive is important when using a silicone material for the distal pad 5 due to its high temperature material. The distal pad 5 is made from a soft material, such as silicone, to mimic the flesh of a real finger pad. The distal pad 5 is attached to the distal phalange 1 by means of the distal pad platform 4. The distal pad platform 4 is secured to the distal platform fastener 11 of the distal phalange 1. In the preferred embodiment of the present invention, the distal platform fastener 11 is a distal platform latch and the distal pad platform 4 comprises of a corresponding latch hole. However, in other embodiments of the present invention, the distal platform fastener 11 can be simply be an adhesive. The distal platform fastener 11 is positioned on a lower distal surface of the distal phalange 1. In comparison to a real finger, the positioning of the distal platform fastener 11 allows the distal pad 5 to be positioned where the finger pads of a real finger would be. The distal phalange 1, the distal pad 5, and the distal pad platform 4 combine together to be shaped like a real finger tip. On the rear end of the distal phalange 1 is the middle phalange joint channel 12. The middle phalange joint channel 12 is a hole that laterally traverses through the distal phalange 1. The middle phalange joint channel 12 provides a pivot point for the connection of the middle phalange 2. The pair of proximal pulling hinges 13 is a pair of hinge channels that downwardly extends at an angle from the rear of the distal phalange 1. The pair of proximal pulling hinges 13 are positioned adjacent to the middle phalange joint channel 12. The pair of proximal pulling hinges 13 provides a pulling point for the proximal phalange ring 3 to pull on to mimic the curling motion of a real finger.

In reference to FIGS. 1-3, the middle phalange 2 comprises a middle platform fastener 21, a pair of distal joint hinges 22, a pair of proximal joint hinges 23, and a pair of spring hinge ports 24. For a finger amputee with a missing finger tip, the middle phalange 2 is a frame that wraps around the intermediate phalange of the user's residual finger. The middle pad 7 and the middle pad platform 6 are secured to the middle phalange 2. The middle pad 7 is engaged and adhered to the middle pad platform 6 by a RTV silicone adhesive. Similar to the distal pad 5, the middle pad 7 is made from a soft material, such as silicone. The middle pad 7 is attached to the middle phalange 2 by means of the middle pad platform 6. The middle pad platform 6 is secured to the middle platform fastener 21 of the middle phalange 2. In the preferred embodiment of the present invention, similar to the distal platform fastener 11, the middle platform fastener 21 is a middle platform latch and the middle pad platform 6 comprises of a corresponding latch hole. In other embodiments, the middle platform fastener 21 can be an adhesive. The middle platform fastener 21 is positioned on a lower middle surface of the middle phalange 2. Similar to the distal phalange 1, the positioning of the middle platform fastened allows the middle pad 7 to be positioned where the finger pads of the intermediate phalange of a real finger would be. The middle phalange 2, the middle pad 7, and the middle pad platform 6 combine together to be shaped like a real intermediate phalange. The pair of distal joint hinges 22 is forwardly extended from the middle phalange 2 in parallel relationship to each other. The pair of proximal joint hinges 23 is extended from the middle phalange 2 in an opposite direction of the pair of distal joint hinges 22. As a result, the pair of distal joint hinges 22 and the pair of proximal joint hinges 23 are positioned on opposite ends of the middle phalange 2. The middle phalange 2 is able to jointly connect the distal phalange 1 to the proximal phalange ring 3 together by means of the pair of distal joint hinges 22 and the pair of proximal joint hinges 23.

In reference to FIGS. 1-3, the proximal phalange ring 3 is a two part component comprising of a proximal phalange yoke 31 and a proximal phalange frame 32. The proximal phalange frame 32 is the body of the proximal phalange ring 3 that anchors itself onto the user's finger. The proximal phalange yoke 31 is the brace of the proximal phalange ring 3 that provides support in the motion provided by the present invention. The proximal phalange yoke 31 further comprises, a pair of extending spring hinges 311, a pair of frame joint hinges 312, and a finger base brace 313. The proximal phalange frame 32 comprises an extended wishbone hinge 321, a pair of posterior yoke joint hinge, and a pair of anterior phalange joint hinge 323. The finger base brace 313 is a circular frame that is the body of the proximal phalange yoke 31. The finger base brace 313 is shaped to fit the base of the user's residual finger. The pair of frame joint hinges 312 is extended from the finger base brace 313. The pair of extending spring hinges 311 is a flat spring hinge that extends from tom the pair of frame joint hinges 312. The extended wishbone bone is shaped like a wishbone and is forwardly extending from the proximal phalange frame 32. The pair of anterior phalange joint hinge 323s is extended from the proximal phalange frame 32 adjacent to the extended wishbone hinge 321. The pair of posterior yoke joint holes 322 are holes that laterally traverse through the proximal phalange. The proximal phalange yoke 31 is jointly connected to the proximal phalange frame 32. The pair of frame joint hinges 312 is aligned and engaged to the pair of posterior yoke joint holes 322. The pair of frame join hinges is able to jointly connect to the pair of posterior yoke joint holes 322 by means of a yoke stud. The yoke stud is inwardly protruding from each of the frame joint hinges. The proximal phalange yoke 31 is then aligned and jointly secured to the pair of posterior yoke joint holes 322.

In reference to FIGS. 1-3, the distal phalange 1 is connected to the middle phalange 2. The proximal phalange ring 3 is connected to the middle phalange 2 opposite of the distal phalange 1. The plurality of rods 8 is traversed through the pair of distal joint hinges 22, the middle phalange joint channel 12, the pair of proximal joint hinges 23, the pair of extending spring hinges 311, the extended wishbone hinge 321, and the pair of proximal pulling hinge for the assembly. The plurality of rods 8 consists of a first rod, a second rod, and a third rod. The pair of distal joint hinges 22 is aligned and secured to the middle phalange joint channel 12 by the first rod. The pair of spring hinge ports 24 is aligned and secured to the pair of extending spring hinges 311 by the second rod. The extended wishbone hinge 321 is aligned and secured to the pair of proximal pulling hinges 13 by the third rod. The extended wishbone is extended over and traversed through the middle phalange 2 for its connection to the pair of proximal pulling hinges 13. Each of the anterior phalange joint hinges 323 comprises a middle stud. The middle stud is an outwardly protruding stud from each anterior phalange joint hinge 323. The pair of anterior phalange joint hinges 323 is aligned and jointly secured to the pair of proximal joint hinges 23 by the middle stud. All of the joint connections described provides the prosthetic finger the ability to curl and move like a real finger.

Figure 4:
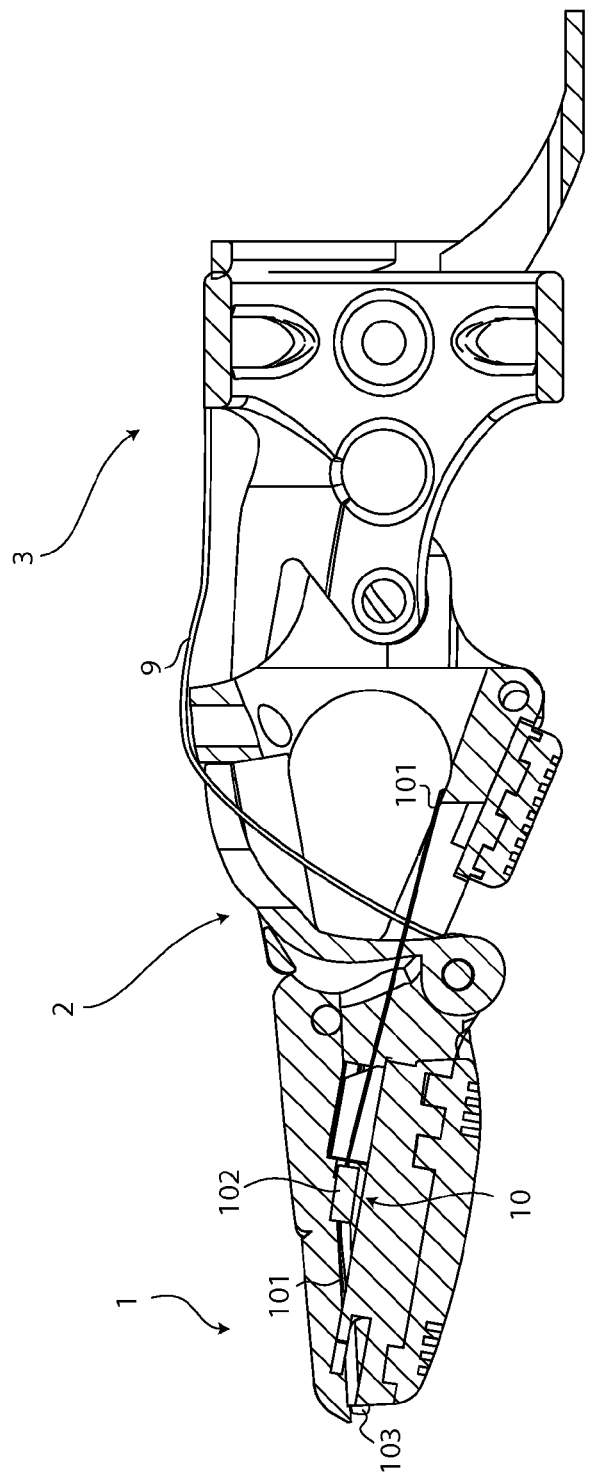
FIG. 4 is a cross sectional view of the present invention showing the articulation cable and the touch screen mechanism.

In reference to FIG. 4, the articulation cable 9 is connected to the proximal phalange frame 32 and the lower distal surface. The articulation cable 9 is traversed through the middle phalange 2 and contributes the life-like natural movements of the prosthetic finger. The touch screen mechanism 10 comprises a conductive thread 101, and a conductive loop 103. The conductive thread 101 consists of made out of a conductive material such as metal. The conductive loop 103 is the portion of the touch screen mechanism 10 that is used by the user to interact with the touch screen. The conductive loop 103 is made from a conductive material similar to the conductive thread 101. The conductive loop 103 is connected directly to the conductive thread 101. The conductive loop 103 is able to provide the user with the ability to interact with a touch screen at different angles. The distal phalange 1 having two holes and two channels is able to allow the conductive loop wrap around the tip of the distal phalange 1. The two holes are positioned on a first distal corner and a second distal corner. Each of the holes are connected a respective channel. The conductive loop 103 is traversed through the two channels and connects to the second thread. The conductive loop 103 is left with an expose segment on the tip of the distal phalange 1 for interaction with a touch screen. To ensure that the touch screen mechanism 10 fully draws the user's natural body current, the conductive thread 101 can be connected to the finger base brace 313 to ensure contact with the user's flesh. In other embodiments of the present invention, the conductive thread 101 can be connected anywhere on the prosthetic finger as long as it makes contact with a user's flesh.

The present invention provides a comfortable and natural movement for a user with an amputated finger. The design can be individually customized for users with varying amounts of lose on their finger. To further provide better aesthetics, the present invention can be coated with colorings to match the user's skin. The ease of use is another advantage of the present invention. To use the present invention, the user can simply slide the prosthetic finger onto the appropriate finger like a ring. To curl and bend the prosthetic finger the used can utilize the natural movements of the residual finger that the device is being worn on. The finger segments will articulate using the same cognitive process that was previously utilized for their original finger. Each of the prosthetic fingers can be independently operated. This means the user will be able to perform the activities including full typing, playing a musical instrument, or anything that requires the full dexterity of a hand. The present invention is fully powered by the user's own body. Each components of the prosthetic finger is able to move simply based on the actions of the user's residual finger. The present invention is designed to offer strength in the lowest profile design. As a result, the present invention naturally conforms with the looks of the user's hand.

Medical benefits of the present invention include uses of the device that reduce swelling and increases circulation, supporting the adjacent finger joints. The present device can be made out of Titanium, Stainless Steel, Aluminum, Silicone, Carbon Fiber, Nylon, Plastic, Wood, Rubber, Gold, Silver, Tungsten, Flex Cable, neoprene or any suitable structural material that is non-irritating to human skin. However, in the preferred embodiment of the present invention, the device is made from the material Duraform EX polymer material.

In another embodiment of the present invention, portions of the prosthetic finger can be used for differing conditions of the user. The present invention can be accommodated for finger tips or full fingers. The extended wishbone hinge 321 can be removed so that the prosthetic finger can be used as joint brace. Additionally, using biocompatible materials, the present invention can be applied as an orthopedic implant. Depending on the condition of the user, the present invention can be surgically implanted into the user's fingers. The use of the surgical implantation of the present invention can be applied for users having injuries that have crushed their bones without the ability to heal and be repaired. As a result, the present invention is able to take the place of the user's original bones without the need for amputation.

Although the invention has been explained in relation to its preferred embodiment, it is to be understood that many other possible modifications and variations can be made without departing from the spirit and scope of the invention as hereinafter claimed.

What is claimed is:

1. A mechanical prosthetic finger device comprises,
   a distal phalange;
   a middle phalange;
   a proximal phalange ring;
   a distal pad platform;
   a distal pad;
   a middle pad platform;
   a middle pad;
   a plurality of rods;
   the distal phalange comprises a distal platform fastener, a middle phalange joint channel, pair of proximal pulling hinges;
   a middle phalange comprises a middle platform fastener, a pair of distal joint hinges, a pair of proximal joint hinges, and a pair of spring hinge ports;
   the proximal phalange ring comprises a proximal phalange yoke and a proximal phalange frame;
   the proximal phalange yoke comprises a pair of extending spring hinges, a pair of frame joint hinges, and a finger base brace;
   the proximal phalange frame comprises an extended wishbone hinge, a pair of posterior yoke joint hinge, a pair of anterior phalange joint hinge;
   the distal pad being adhered to the distal pad platform;
   the middle pad being adhered to the middle pad platform;
   the distal pad platform being secured to the distal platform fastener; and
   the middle pad platform being secured to the middle platform fastener.

2. The mechanical prosthetic finger device as claimed in claim 1 comprises,
   the distal platform fastener being positioned on a lower distal surface of the distal phalange;
   the middle phalange joint channel being a hole traversing through a rear end of the distal phalange; and
   the pair of proximal pulling hinges being rearward and downwardly extending from the distal phalange and being positioned adjacent to the middle phalange joint channel.

3. The mechanical prosthetic finger device as claimed in claim 1 comprises,
   the middle platform fastener being positioned on a lower middle surface of the middle phalange;
   the pair of distal joint hinges being extended from the middle phalange in parallel relationship to each other; and
   the pair of proximal joint hinges being extended from the middles phalange opposite of the pair of distal joint hinges.

4. The mechanical prosthetic finger device as claimed in claim 1 comprises,
   the proximal phalange yoke being jointly connected to the proximal phalange frame; and
   the pair of frame joint hinges being aligned and engaged to the pair of posterior yoke joint holes.

5. The mechanical prosthetic finger device as claimed in claim 4 comprises,
   the finger base brace being a circular frame, wherein the finger base brace is shaped to fit the base of a finger;
   the pair of extending spring hinges being extended from the pair of frame joint hinges; and
   the pair of frame joint hinges being extended the finger base brace.

6. The mechanical prosthetic finger device as claimed in claim 4 comprises,
   the extended wishbone hinge being extended from the proximal phalange frame;
   the pair of anterior phalange joint hinge being extended from the proximal phalange frame adjacent to the extended wishbone hinge; and
   the pair of posterior yoke joint holes being traversed through the proximal phalange frame.

7. The mechanical prosthetic finger device as claimed in claim 1 comprises,
   the distal phalange being connected to the middle phalange;
   the proximal phalange ring 3 being connected to the middle phalange opposite of the distal phalange;
   the plurality of rods being traversed through the pair of distal joint hinges, the middle phalange joint channel, the pair of proximal joint hinges, the pair of extending spring hinges, the extended wishbone hinge, and the pair of proximal pulling hinges;
   wherein the plurality of rods consists of a first rod, a second rod, and a third rod;
   the pair of distal joint hinges being aligned and secured to the middle phalange joint channel by the first rod;
   the pair of spring hinge ports being aligned and secured to the pair of extending spring hinges by the second rod;
   the extended wishbone hinge being aligned and secured to the pair of proximal pulling hinges by the third rod; and
   the extended wishbone being traversed through the middle phalange.

8. The mechanical prosthetic finger device as claimed in claim 7 comprises, wherein each anterior phalange joint hinge comprises a middle stud;
the middle stud being outwardly protruding from each anterior phalange joint hinge; and
the pair of anterior phalange joint hinges being aligned and jointly secured to the pair of proximal joint hinges by the middle stud.

9. The mechanical prosthetic finger device as claimed in claim 7 comprises,
wherein each frame joint hinge comprises a yoke stud;
the yoke stud being inwardly protruding from each frame joint hinge; and
the proximal phalange yoke being aligned and jointly secured to the pair of posterior yoke joint holes.

10. A mechanical prosthetic finger device comprises,
a distal phalange;
a middle phalange;
a proximal phalange ring;
a distal pad platform;
a distal pad;
a middle pad platform;
a middle pad;
a plurality of rods;
a touch screen mechanism;
an articulation cable;
the distal phalange comprises a distal platform fastener, a middle phalange joint channel, pair of proximal pulling hinges;
a middle phalange comprises a middle platform fastener, a pair of distal joint hinges, a pair of proximal joint hinges, and a pair of spring hinge ports;
the proximal phalange ring comprises a proximal phalange yoke and a proximal phalange frame;
the proximal phalange yoke comprises a pair of extending spring hinges, a pair of frame joint hinges, and a finger base brace;
the proximal phalange frame comprises an extended wishbone hinge, a pair of posterior yoke joint hinge, a pair of anterior phalange joint hinge;
the distal pad being adhered to the distal pad platform;
the middle pad being adhered to the middle pad platform;
the distal pad platform being secured to the distal platform fastener; and
the middle pad platform being secured to the middle platform fastener.

11. The mechanical prosthetic finger device as claimed in claim 10 comprises,
the distal platform fastener being positioned on a lower distal surface of the distal phalange;
the middle phalange joint channel being a hole traversing through a rear end of the distal phalange;
the pair of proximal pulling hinges being rearward and downwardly extending from the distal phalange and being positioned adjacent to the middle phalange joint channel;
the middle platform fastener being positioned on a lower middle surface of the middle phalange;
the pair of distal joint hinges being extended from the middle phalange in parallel relationship to each other; and
the pair of proximal joint hinges being extended from the middles phalange opposite of the pair of distal joint hinges.

12. The mechanical prosthetic finger device as claimed in claim 10 comprises,
the proximal phalange yoke being jointly connected to the proximal phalange frame; and
the pair of frame joint hinges being aligned and engaged to the pair of posterior yoke joint holes by a rod.

13. The mechanical prosthetic finger device as claimed in claim 12 comprises,
the finger base brace being a circular frame, wherein the finger base brace is shaped to fit the base of a finger;
the pair of extending spring hinges being extended from the pair of frame joint hinges;
the pair of frame joint hinges being extended the finger base brace;
the extended wishbone hinge being extended from the proximal phalange frame;
the pair of anterior phalange joint hinge being extended from the proximal phalange frame adjacent to the extended wishbone hinge; and
the pair of posterior yoke joint holes being traversed through the proximal phalange frame.

14. The mechanical prosthetic finger device as claimed in claim 10 comprises,
the distal phalange being connected to the middle phalange;
the proximal phalange ring being connected to the middle phalange opposite of the distal phalange;
the plurality of rods being traversed through the pair of distal joint hinges, the middle phalange joint channel, the pair of proximal joint hinges, the pair of extending spring hinges, the extended wishbone hinge, and the pair of proximal pulling hinges;
wherein the plurality of rods consists of a first rod, a second rod, and a third rod;
the pair of distal joint hinges being aligned and secured to the middle phalange joint channel by the first rod;
the pair of spring hinge ports being aligned and secured to the pair of extending spring hinges by the second rod;
the extended wishbone hinge being aligned and secured to the pair of proximal pulling hinges by the third rod; and
the extended wishbone being traversed through the middle phalange.

15. The mechanical prosthetic finger device as claimed in claim 14 comprises,
wherein each anterior phalange joint hinge comprises a middle stud;
the middle stud being outwardly protruding from each anterior phalange joint hinge;
the pair of anterior phalange joint hinges being aligned and jointly secured to the pair of proximal joint hinges by the middle stud;
wherein each frame joint hinge comprises a yoke stud;
the yoke stud being inwardly protruding from each frame joint hinge; and
the proximal phalange yoke being aligned and jointly secured to the pair of posterior yoke joint holes.

16. The mechanical prosthetic finger device as claimed in claim 11 comprises,
the articulation cable being connected to the proximal phalange frame and the lower distal surface and being traversed through the middle phalange;
the touch screen mechanism comprises a conductive thread, and a conductive loop;
the distal phalange having two channels and two holes;
the two holes being positioned on a first distal tip corner and a second distal tip corner leading into the two channels;
the conductive loop being traversed through the two channels, wherein the conductive loop is looped through the two channels multiple times; and the conductive loop being connected to the finger base brace.

17. A mechanical prosthetic finger device comprises,
a distal phalange;
a middle phalange;
a proximal phalange ring;
a distal pad platform;
a distal pad;
a middle pad platform;
a middle pad;
a plurality of rods;
a touch screen mechanism;
an articulation cable;
the distal phalange comprises a distal platform fastener, a middle phalange joint channel, pair of proximal pulling hinges;
a middle phalange comprises a middle platform fastener, a pair of distal joint hinges, a pair of proximal joint hinges, and a pair of spring hinge ports;
the proximal phalange ring comprises a proximal phalange yoke and a proximal phalange frame;
the proximal phalange yoke comprises a pair of extending spring hinges, a pair of frame joint hinges, and a finger base brace;
the proximal phalange frame comprises an extended wishbone hinge, a pair of posterior yoke joint hinge, a pair of anterior phalange joint hinge;
the distal pad being adhered to the distal pad platform;
the middle pad being adhered to the middle pad platform;
the distal pad platform being secured to the distal platform fastener;
the middle pad platform being secured to the middle platform fastener;
the distal platform fastener being positioned on a lower distal surface of the distal phalange;
the middle phalange joint channel being a hole traversing through a rear end of the distal phalange;
the pair of proximal pulling hinges being rearward and downwardly extending from the distal phalange and being positioned adjacent to the middle phalange joint channel;
the middle platform fastener being positioned on a lower middle surface of the middle phalange;
the pair of distal joint hinges being extended from the middle phalange in parallel relationship to each other;
the pair of proximal joint hinges being extended from the middles phalange opposite of the pair of distal joint hinges;
the proximal phalange yoke being jointly connected to the proximal phalange frame; and
the pair of frame joint hinges being aligned and engaged to the pair of posterior yoke joint holes by a rod.

18. The mechanical prosthetic finger device as claimed in claim 17 comprises,
the finger base brace being a circular frame, wherein the finger base brace is shaped to fit the base of a finger;
the pair of extending spring hinges being extended from the pair of frame joint hinges;
the pair of frame joint hinges being extended the finger base brace;
the extended wishbone hinge being extended from the proximal phalange frame;
the pair of anterior phalange joint hinge being extended from the proximal phalange frame adjacent to the extended wishbone hinge; and
the pair of posterior yoke joint holes being traversed through the proximal phalange frame.

19. The mechanical prosthetic finger device as claimed in claim 17 comprises,
the distal phalange being connected to the middle phalange;
the proximal phalange ring being connected to the middle phalange opposite of the distal phalange;
the plurality of rods being traversed through the pair of distal joint hinges, the middle phalange joint channel, the pair of proximal joint hinges, the pair of extending spring hinges, the extended wishbone hinge, and the pair of proximal pulling hinges;
wherein the plurality of rods consists of a first rod, a second rod, and a third rod;
the pair of distal joint hinges being aligned and secured to the middle phalange joint channel by the first rod;
the pair of spring hinge ports being aligned and secured to the pair of extending spring hinges by the second rod;
the extended wishbone hinge being aligned and secured to the pair of proximal pulling hinges by the third rod; and
the extended wishbone being traversed through the middle phalange.

20. The mechanical prosthetic finger device as claimed in claim 17 comprises,
wherein each anterior phalange joint hinge comprises a middle stud;
the middle stud being outwardly protruding from each anterior phalange joint hinge;
the pair of anterior phalange joint hinges being aligned and jointly secured to the pair of proximal joint hinges by the middle stud;
wherein each frame joint hinge comprises a yoke stud;
the yoke stud being inwardly protruding from each frame joint hinge; and
the proximal phalange yoke being aligned and jointly secured to the pair of posterior yoke joint holes.

* * * * *